(12) United States Patent
Kawamura et al.

(10) Patent No.: US 12,059,521 B2
(45) Date of Patent: Aug. 13, 2024

(54) AIR TRAP CHAMBER AND EXTRACORPOREAL CIRCULATION CIRCUIT

(71) Applicant: NIKKISO CO., LTD., Tokyo (JP)

(72) Inventors: Shunsuke Kawamura, Makinohara (JP); Shunichi Koda, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 962 days.

(21) Appl. No.: 17/050,768

(22) PCT Filed: Mar. 15, 2019

(86) PCT No.: PCT/JP2019/010960
§ 371 (c)(1),
(2) Date: Oct. 26, 2020

(87) PCT Pub. No.: WO2019/211951
PCT Pub. Date: Nov. 7, 2019

(65) Prior Publication Data
US 2021/0093774 A1    Apr. 1, 2021

(30) Foreign Application Priority Data
May 2, 2018   (JP) .................................. 2018-088657

(51) Int. Cl.
*A61M 1/36*   (2006.01)
*A61M 1/38*   (2006.01)

(52) U.S. Cl.
CPC ........ *A61M 1/3627* (2013.01); *A61M 1/3607* (2014.02); *A61M 1/3638* (2014.02); *A61M 1/38* (2013.01)

(58) Field of Classification Search
CPC ..... A61M 1/3638; A61M 1/3607; A61M 1/38
See application file for complete search history.

(56) References Cited

U.S. PATENT DOCUMENTS

| 5,591,251 A    | 1/1997  | Brugger |
| 2002/0177786 A1 | 11/2002 | Balbo |

(Continued)

FOREIGN PATENT DOCUMENTS

| EP | 3266477 A1 | 1/2018 |
| EP | 3326670 A1 | 5/2018 |

(Continued)

OTHER PUBLICATIONS

Jun. 5, 2023 Office Action issued in Chinese Patent Application No. 201980028249.4.

(Continued)

*Primary Examiner* — Rebecca E Eisenberg
*Assistant Examiner* — Kate Elizabeth Strachan
(74) *Attorney, Agent, or Firm* — Oliff PLC

(57) ABSTRACT

A chamber body is provided, as regions where the liquid flows, with: an upper region including an area from the inner surface of the upper wall to the introduction pipe; a lower region connected to the outlet port; and a connection region connecting the upper region and the lower region. The inner circumferential surface of the upper region has a larger diameter than the inner circumferential surface of the lower region. As a result of diameter reduction from the connection portion relative to the upper region to the connection portion relative to the lower region, an inclined surface is formed on the inner circumferential surface of the connection region.

8 Claims, 16 Drawing Sheets

(56) References Cited

U.S. PATENT DOCUMENTS

| | | | |
|---|---|---|---|
| 2003/0006187 A1 | 1/2003 | Frey | |
| 2006/0173395 A1* | 8/2006 | Brugger | A61M 1/3621 |
| | | | 604/6.09 |
| 2008/0269681 A1* | 10/2008 | Kavazov | A61M 5/1413 |
| | | | 604/123 |
| 2011/0190700 A1* | 8/2011 | Kavazov | A61M 5/385 |
| | | | 604/152 |
| 2015/0182683 A1 | 7/2015 | Spickermann et al. | |
| 2018/0221559 A1 | 8/2018 | Ritter | |

FOREIGN PATENT DOCUMENTS

| | | | | |
|---|---|---|---|---|
| JP | 3105777 B2 * | 11/2000 | | G06F 21/10 |
| JP | 2002-525192 A | 8/2002 | | |
| JP | 3105777 U | 11/2004 | | |
| JP | 2012-095842 A | 5/2012 | | |
| JP | 2012095842 A * | 5/2012 | | |
| JP | 5931128 B2 | 6/2016 | | |
| JP | 2016119949 A * | 7/2016 | | |
| JP | 2016-158921 A | 9/2016 | | |
| WO | WO-2012072029 A1 * | 6/2012 | | B01D 15/14 |

OTHER PUBLICATIONS

Dec. 8, 2021 Extended European Search Report issued in European Patent Application No. 19796954.6.
Oct. 21, 2022 Office Action issued in Chinese Patent Application No. 201980028249.4.

* cited by examiner

AIR TRAP CHAMBER AND EXTRACORPOREAL CIRCULATION CIRCUIT

TECHNICAL FIELD

The present invention relates to an air trap chamber, and to an extracorporeal circulation circuit including the same.

BACKGROUND

For instance, in hemodialysis, blood removed from a patient is sent to an extracorporeal circulation circuit. The extracorporeal circulation circuit includes an arterial side circuit to which the removed blood is supplied, a purifier (dialyzer) that purifies the blood sent from the arterial side circuit, and a venous side circuit that returns the purified blood to the patient. At least one of the arterial side circuit and the venous side circuit is provided with an air trap chamber for capturing bubbles (debubbling) in blood flowing through the circuit.

The priming volume, the amount of blood removed from a patient and sent to an extracorporeal circulation circuit, is preferably made small in order to reduce the burden on the patient. A way of reducing the priming volume is to reduce the volumetric capacity of the air trap chamber. However, if the volumetric capacity of the air trap chamber is extremely small, bubbles may remain on the blood flow; that is, the force of the flow may exceed the buoyancy acting on the bubbles, so that the bubbles may leave the air trap chamber together with the blood.

Therefore, in Patent Document 1, for example, a receiving surface extending in a direction orthogonal to the blood flow is provided immediately below the blood inlet, and the action of blood hitting on the hitting surface changes the direction of the blood flow. Changing the flow of blood in the air trap chamber in this way increases the moving distance in the air trap chamber, and accordingly allows bubbles to be captured more easily.

CITATION LIST

Patent Literature

Patent Document 1: JP 2016-158921 A

SUMMARY

Technical Problem

Incidentally, when the hitting surface is placed so as to be orthogonal to the blood flow, the flow velocity declines because the blood flow hits the hitting surface. Then, blood is retained in the air trap chamber. In particular, the retention becomes remarkable in the sidestream region away from the mainstream.

It is therefore an advantage of the present invention to provide an air trap chamber capable of changing the flow direction of the liquid in the air trap chamber while suppressing a decrease in the force of the liquid flow.

Solution to Problem

The present invention relates to an air trap chamber. The air trap chamber includes a chamber body and an inlet pipe. The chamber body that has a generally cylindrical shape and has one end defined with respect to a central axis and covered with a top wall having an inlet, and the other end having an outlet, so that a liquid flows down from the inlet to the outlet. The inlet pipe extends from the inlet into the chamber body, and has an ejection port being an end opening and provided in the inner peripheral surface of the chamber body facing in a circumferential direction. The chamber body has the following regions in which liquid flows: an upper region extending from the top wall inner surface to the inlet pipe, a lower region connected to the outlet, and a connection region connecting the upper region and the lower region. The inner peripheral surface of the upper region has a larger diameter than does the inner peripheral surface of the lower region, and the inner peripheral surface of the connection region has an inclined surface formed by reducing the diameter from a point of connection to the upper region to a point of connection to the lower region.

According to the aforementioned invention, the liquid is ejected from the ejection port along the inner peripheral surface of the chamber body. The flow of the ejected liquid becomes a swirl flow along the inner peripheral surface of the chamber body, and heads for the outlet. Here, since the inner peripheral surface of the connection region is an inclined surface, the direction of at least part of the swirl flow can be changed along the inclined surface. Since the inclined surface is formed along the direction of the swirl flow, the force of the liquid flow is maintained even when the flow direction is changed.

In the aforementioned invention, the inner peripheral surface of the connection region may have an oblique circular truncated cone shape having a vertical surface parallel with the inner peripheral surface of the upper region.

Since the inner peripheral surface of the connection region has an oblique circular truncated cone shape that includes a vertical surface parallel with the inner peripheral surface of the upper region, the inclination increases from the inner peripheral surface of the upper region toward the inclined surface of the connection region along the circumferential direction. With such continuous inclination, the swirl flow along the inner peripheral surface of the upper region smoothly moves to the inclined surface, so that the flow direction can be changed on the inclined surface while the force of the flow is maintained.

In the aforementioned invention, an angle of the inclined surface to a plane perpendicular to the opening axis of the outlet may be greater than 0° and less than 90°.

In the aforementioned invention, an angle of the inclined surface to a plane perpendicular to the opening axis of the outlet may be greater than or equal to 25° and less than or equal to 72°.

When the inclined surface is inclined by an angle in this range, bubble leakage, the phenomenon in which bubbles escape from the outlet, is suppressed.

In the aforementioned invention, the inclined surface may be a concave curved surface projecting radially outward from the central axis of the chamber body.

In the aforementioned invention, the inclined surface may be a convex curved surface projecting radially inward with respect to the central axis of the chamber body.

The present invention also relates to an extracorporeal circulation circuit. The circuit circulates removed blood. The extracorporeal circulation circuit has a flow path to which the air trap chamber according to the aforementioned invention is coupled.

Advantageous Effects of Invention

According to the present invention, the flow direction of the liquid in the air trap chamber can be changed while a decrease in the force of the liquid flow is suppressed.

DESCRIPTION OF EMBODIMENTS

Figure 1:
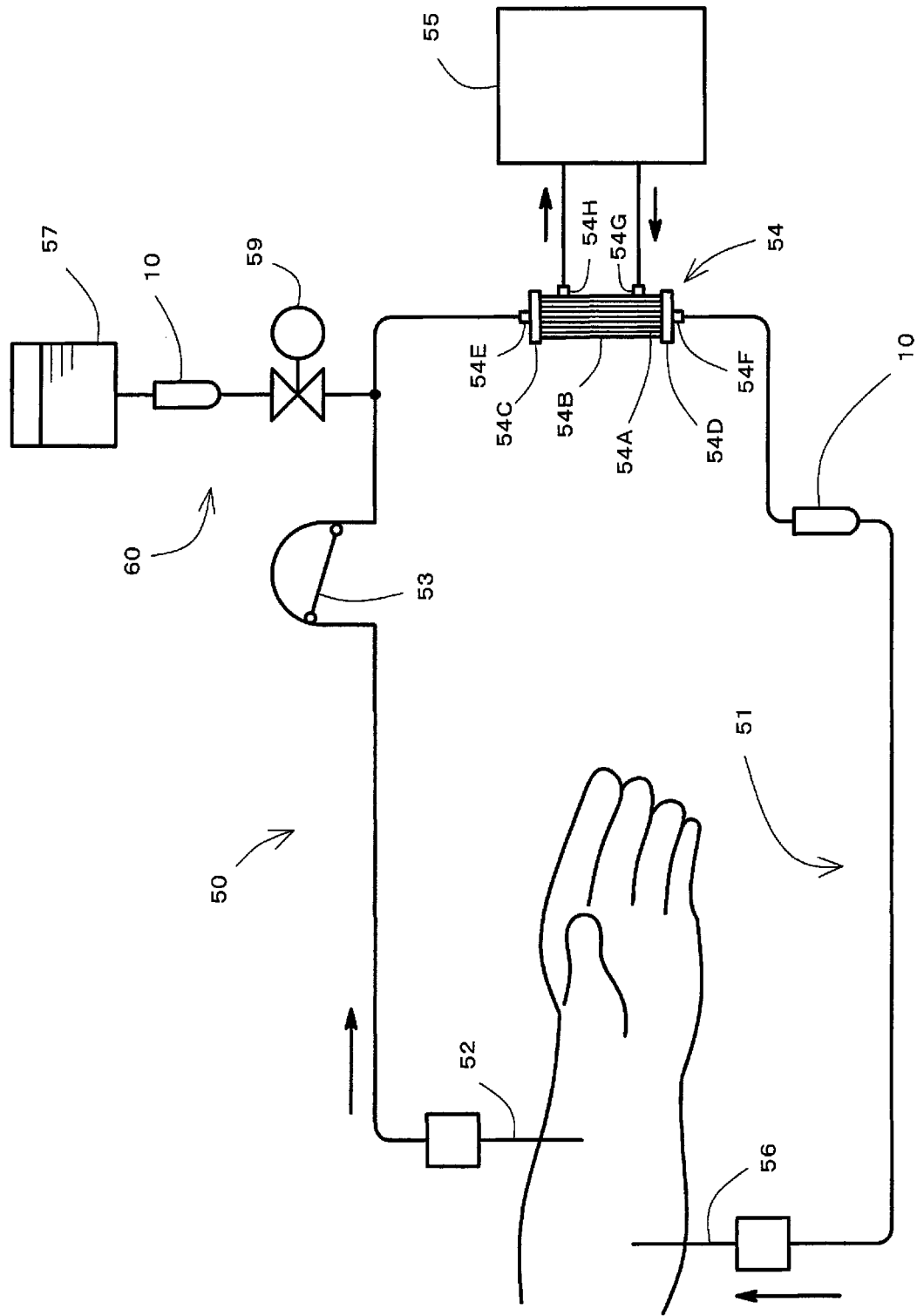
FIG. 1 is a diagram illustrating an extracorporeal circulation circuit using an air trap chamber according to an embodiment.

FIG. 1 illustrates an extracorporeal circulation circuit to which an air trap chamber 10 according to an embodiment is coupled. The extracorporeal circulation circuit is a circuit used for hemodialysis, for example, and includes an arterial side circuit 50, a blood purifier 54, a dialyzer 55, a venous side circuit 51, and a replacement liquid line 60. Note that the air trap chamber 10 according to this embodiment is coupled to the extracorporeal circulation circuit used for dialysis treatment, but this is not necessarily the case. For instance, the air trap chamber 10 according to the embodiment may be coupled to an extracorporeal circulation circuit that can purify a patient's blood. For instance, the air trap chamber 10 according to this embodiment may be coupled to an extracorporeal circulation circuit used in acetate free biofiltration (AFBF), continuous slow hemofiltration therapy, hemadsorption therapy, selective blood cell depletion therapy, simple plasma exchange therapy, double membrane filtration plasma exchange therapy, plasma adsorption therapy, or the like. The air trap chamber 10 according to this embodiment can be provided in the arterial side circuit 50, the venous side circuit 51, and the replacement liquid line 60, which will be described later, of the extracorporeal circulation circuit. In addition, the air trap chamber 10 according to this embodiment can be coupled to a path where thrombosis may occur; that is, an extracorporeal circulation circuit path in which blood or blood components flow. In addition, the air trap chamber 10 according to this embodiment can be coupled to extracorporeal circulation circuit paths in which blood or blood components flow, extracorporeal circulation circuit paths in which saline solution flows, and extracorporeal circulation circuit paths including these.

The arterial side circuit 50 is supplied with blood removed from the patient's body. The arterial side circuit 50 includes an arterial side puncture needle 52 and a roller pump 53 from the upstream side. The arterial side puncture needle 52 is introduced into a blood vessel of the patient and blood is sent to the tube of the arterial side circuit 50 (blood removal).

The roller pump 53 transports the blood in the tube to the blood purifier 54 by externally squeezing the tube. For instance, since the circuit may be filled with a priming liquid from the venous side circuit during priming, the roller pump 53 may be capable of rotating in the forward and reverse directions.

The air trap chamber 10 according to this embodiment may be coupled between the arterial side puncture needle 52 and the roller pump 53 and between the roller pump 53 and the blood purifier 54. The configuration and function of the air trap chamber 10 will be described later. It should be noted that the air trap chamber 10 in the venous side circuit 51 is indispensable to ensure debubbling of the blood to be returned, whereas these air trap chambers 10 provided in the arterial side circuit 50 are optional.

The replacement liquid line 60 is provided between the roller pump 53 and the blood purifier 54 in the arterial side circuit 50. The replacement liquid line 60 is provided with a replacement liquid bag 57 and a clamp 59. The air trap chamber 10 is provided between the replacement liquid bag 57 and the clamp 59.

The replacement liquid bag 57 contains saline solution as a replacement liquid. For instance, during priming of the extracorporeal circulation circuit, the clamp 59 is opened and the saline solution is supplied from the replacement liquid bag 57 to the extracorporeal circulation circuit. Bubbles in the circuit are removed by filling the circuit with saline solution. Upon completion of the priming, the clamp 59 is closed.

Upon completion of the dialysis treatment, the clamp 59 is opened again to return the blood from the circuit to the patient's body, filling the circuit with saline solution from the replacement liquid bag 57. In other words, the blood in the circuit is replaced with saline solution.

The blood purifier 54 purifies the blood sent from the arterial side circuit 50. The blood purifier 54 is a so-called dialyzer, and the dialysate and blood are exchanged through a hollow fiber membrane 54A, for example. In the blood purifier 54, a bundle of the hollow fiber membranes 54A (hollow fiber membrane bundle) is contained in a column 54B.

The column 54B is a cylindrical container member, and has an inlet side cap 54C at one end with respect to the direction of the central axis and an outlet side cap 54D at the other end. The inlet side cap 54C is provided with a blood inlet port 54E coupled to a connector (not shown in the drawing) at the downstream end of the arterial side circuit 50. The outlet side cap 54D is provided with a blood outlet port 54F coupled to a connector (not shown in the drawing) at the upstream end of the venous side circuit 51. Blood sent from the arterial side circuit 50 flows from the blood inlet port 54E into the hollow fiber membranes 54A.

A dialysate inlet port 54G is provided in a portion of the column 54B adjacent to the outlet side cap 54D. A dialysate outlet port 54H is provided in a portion of the column 54B adjacent to the inlet side cap 54C. The dialysate is sent from the dialyzer 55 into the column 54B through the dialysate inlet port 54G. The dialysate and blood are exchanged via the hollow fiber membranes 54A, thereby purifying the blood. The dialysate after the exchange is returned to the dialyzer 55 via the dialysate outlet port 54H. The purified blood is sent to the venous side circuit 51 via the blood outlet port 54F.

In the venous side circuit 51, the purified blood is returned to the patient Ⓢ body via a venous side puncture needle 56. The air trap chamber 10 is provided in the venous side circuit 51 in order to remove bubbles in the blood (debubble) when blood is returned.

Figure 2:
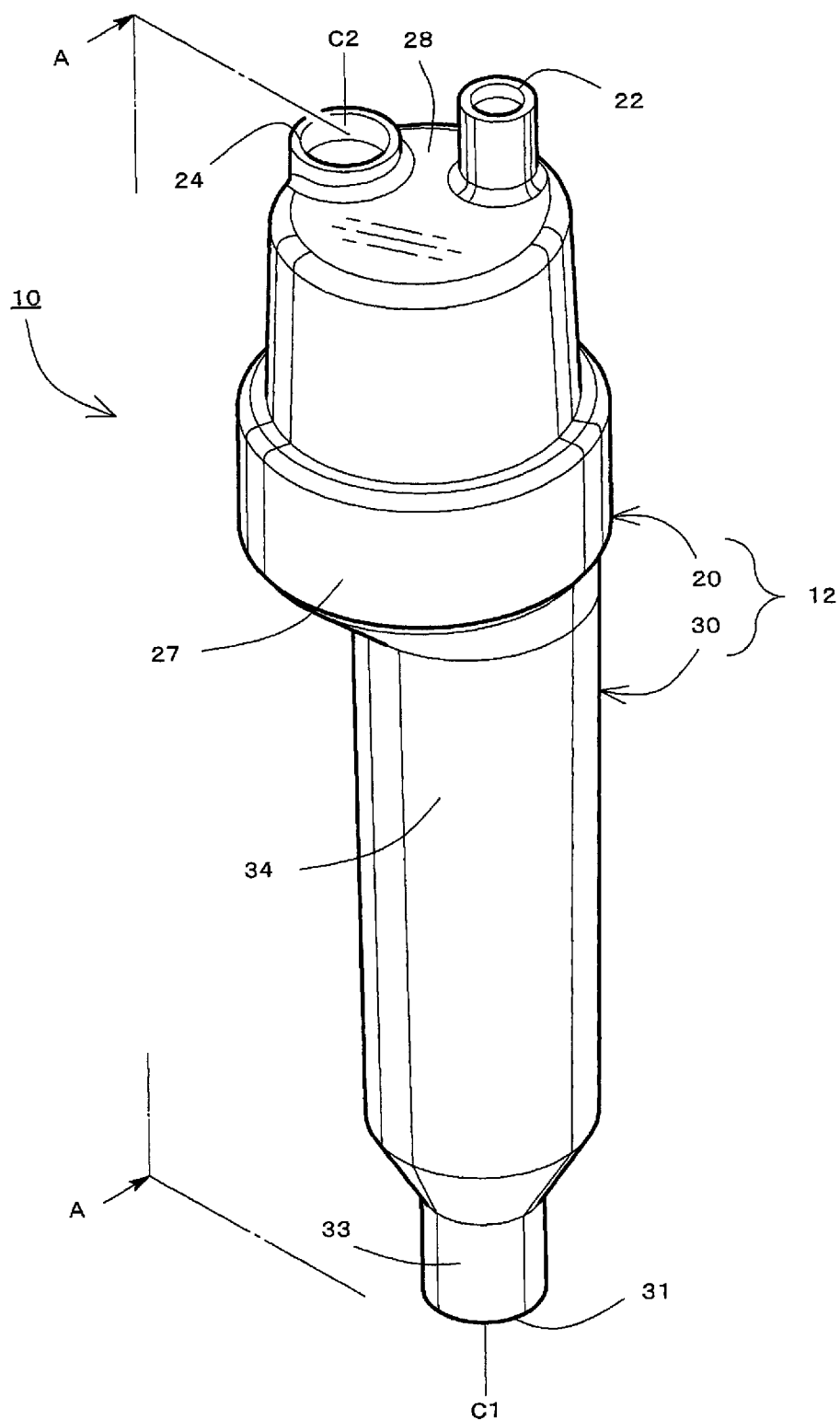
FIG. 2 is a perspective view illustrating an air trap chamber according to the embodiment.
Figure 3:
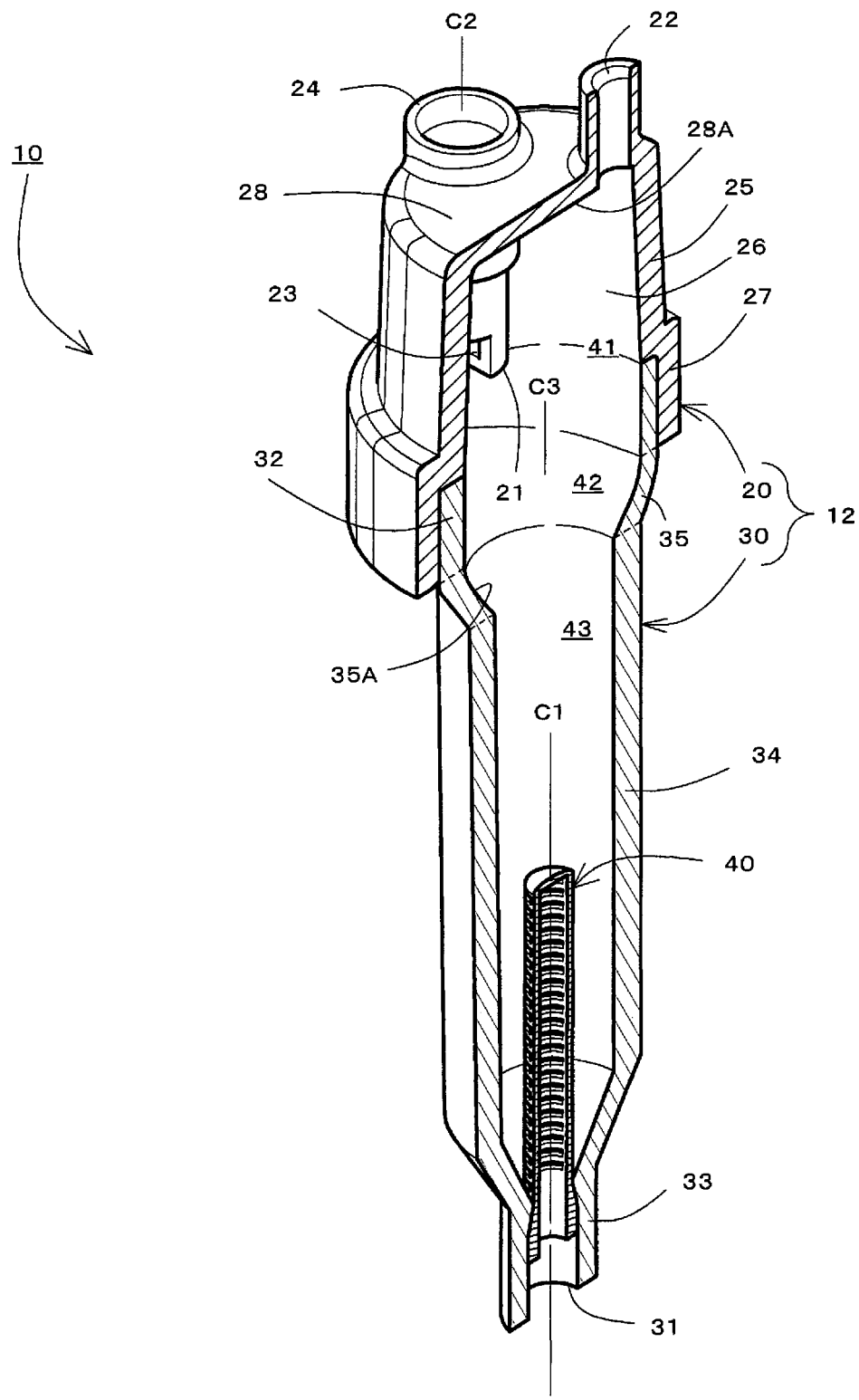
FIG. 3 is a perspective sectional view illustrating an air trap chamber according to the embodiment.

FIG. 2 illustrates the air trap chamber 10 according to this embodiment. FIG. 3 illustrates a perspective sectional view of the air trap chamber 10. The air trap chamber 10 includes a chamber body 12 and a filter 40.

During the dialysis treatment, the air trap chamber 10 is used upright so that its upper side in the drawing is the upper side and its lower side in the drawing is the lower side. Unless otherwise specified, the position and configuration of each component will be explained below with reference to the upright posture during use.

The chamber body 12 has a generally cylindrical shape, and one of its ends (upper end) defined with respect to a central axis C1 is covered with a top wall 28. An inlet 24 and an air vent 22 are provided in the top wall 28. An outlet 31 is provided at the other end (lower end) defined with respect to the central axis C1 of the chamber body 12. In other words, in the chamber body 12, a liquid (for example, blood or saline solution) flows down from the inlet 24 to the outlet 31.

Figure 7:
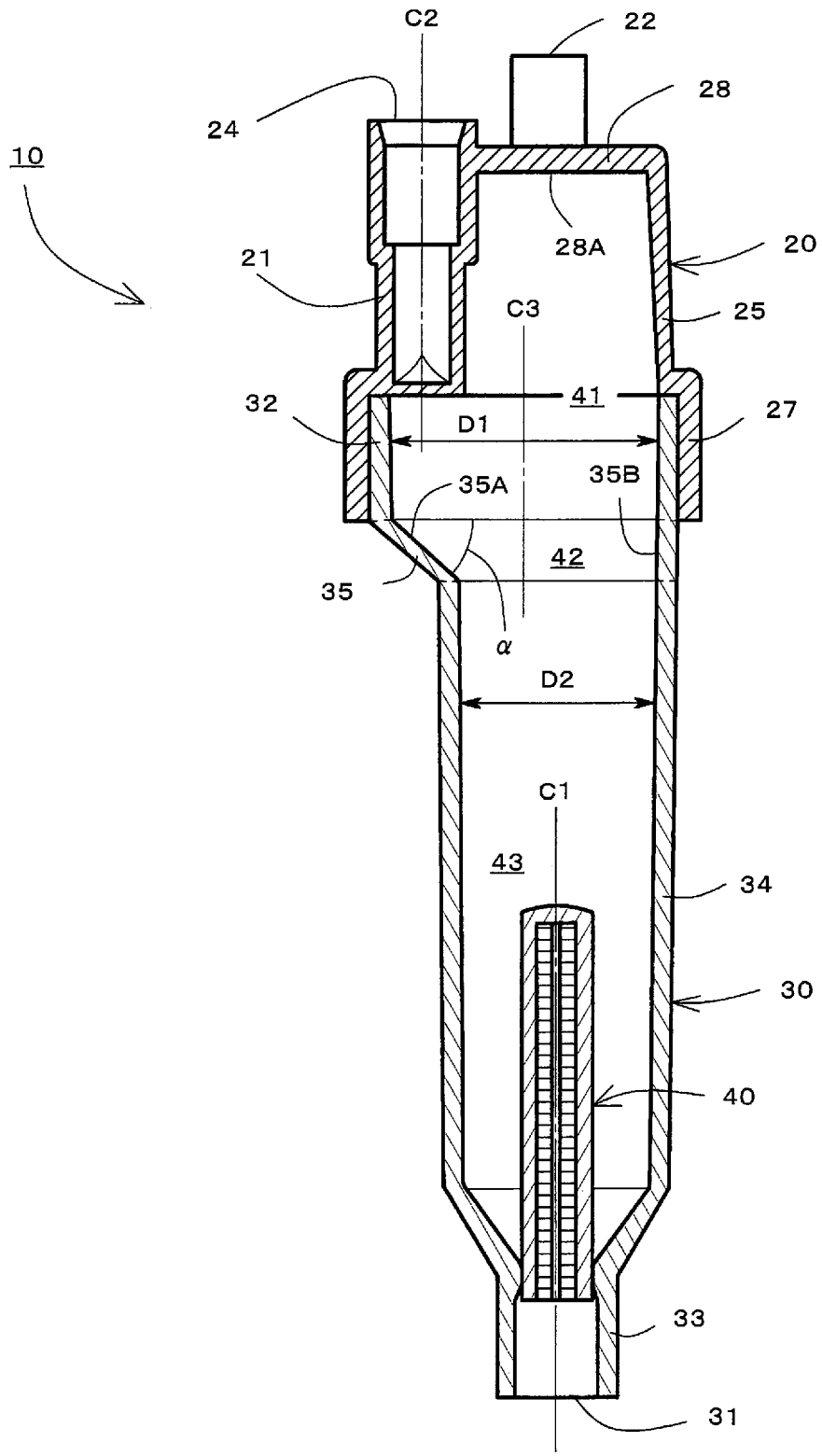
FIG. 7 is a cross-sectional view along line A-A in FIG. 2.

As illustrated in FIG. 7 described later, in the air trap chamber 10 according to this embodiment, an opening axis C2 of the inlet 24, a central axis C3 of first and second connection flanges 27 and 32, and the opening axis C1 of an outlet pipe 33 are not coaxial. Therefore, although any one of the three can be adopted as the central axis of the air trap chamber 10, for convenience, the opening axis C1 of the outlet pipe 33 is defined as the central axis of the air trap chamber 10 in the following cases. Since the opening axes C1 and C2 and the central axis C3 are extended in parallel with each other, no matter which axis is taken as a reference, the positional relationship with one end (upper end) and the other end (lower end) defined with respect to the axes is basically unchanged.

Figure 5:
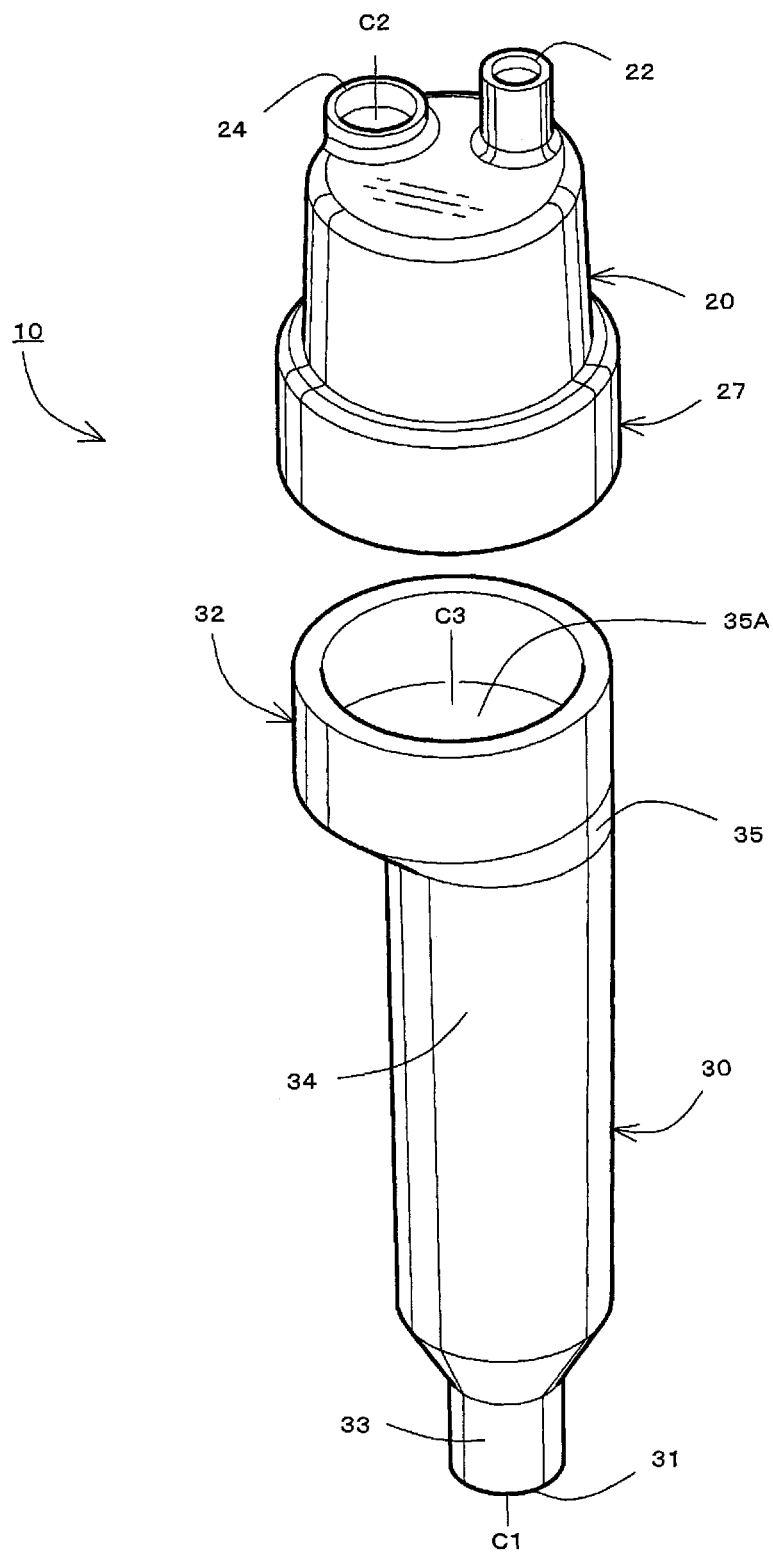
FIG. 5 is a perspective exploded view illustrating an example in which the air trap chamber according to the embodiment is disassembled into a cap and a housing.

As illustrated in FIG. 5, for example, the chamber body 12 may consist of a cap 20 that is an upper member and a housing 30 that is a lower member. The cap 20 and the housing 30 are obtained by, for example, injection molding a resin.

Figure 4:
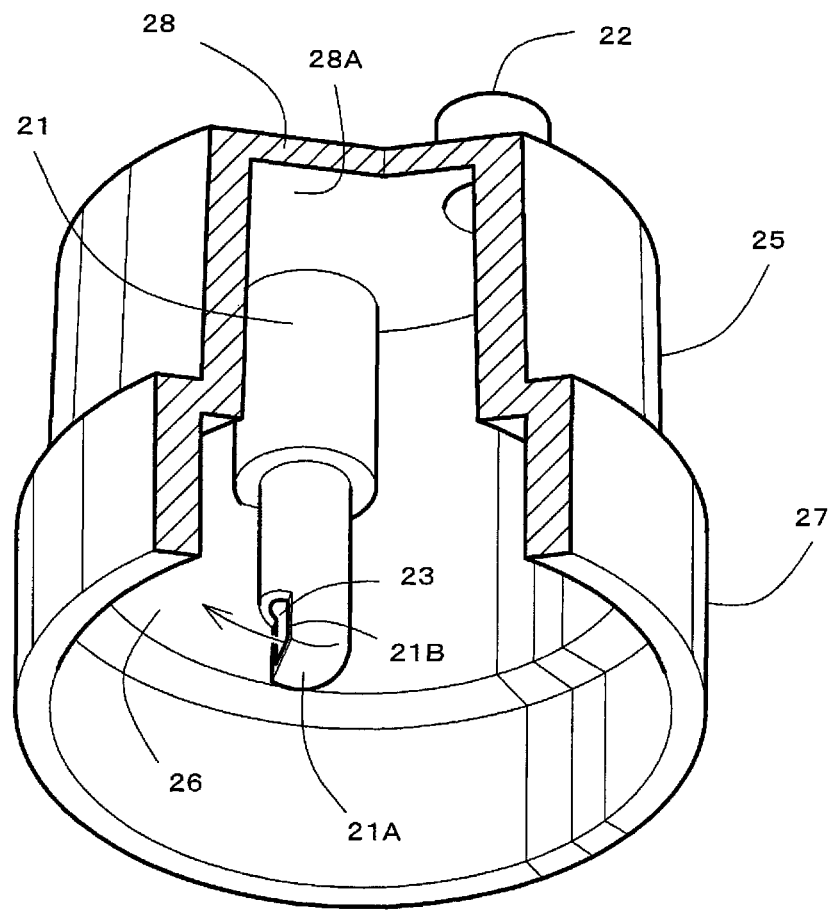
FIG. 4 is a diagram illustrating the configuration of a cap of the air trap chamber according to the embodiment.

FIG. 4 illustrates a perspective sectional view of the cap 20. The cap 20 is a member having a U-shaped cross section and an inlet pipe 21 and the air vent 22 at the upper end (one end). The cap 20 includes the top wall 28, a cap body 25, a first connection flange 27, and the inlet pipe 21.

The cap body 25 is a liquid contact portion whose inner surface is to come into contact with liquid, and has a cylindrical shape in which one end (upper end) of the chamber body 12 defined with respect to the direction of the central axis C1 is closed with the top wall 28. The inlet 24 (see FIG. 3) and the air vent 22 are formed in the top wall 28. The other end (lower end) of the cap body 25 is coupled to the first connection flange 27. The first connection flange 27 is the other end (lower end) of the cap 20 defined with respect to the direction of the central axis C1.

The inlet pipe 21 is extended from the top wall 28 to the inside of the cap body 25; that is, the inside of the chamber body 12. When the air trap chamber 10 is provided in the venous side circuit 51, the inlet 24, which is bonded to the tube on the upstream side of the venous side circuit 51 with a solvent or the like, is formed at the upper end of the inlet pipe 21. An ejection port 23, which ejects liquid into the chamber body 12, is formed at the lower end of the inlet pipe 21. As the ejection port 23 is provided below an inner surface 28A of the top wall 28 in this way, bubble leak, the phenomenon in which bubbles in the chamber body 12 leak from the inlet pipe 21 to the upstream side of the venous side circuit 51, can be prevented.

In other words, for instance, when the ejection port 23 is provided at the inner surface 28A of the top wall 28; that is, at the same height as the air vent 22, the bubbles in the chamber may move to the ejection port 23 without going to the air vent 22, and then leak to the upstream side of the venous side circuit 51. For this reason, in the air trap chamber 10 according to this embodiment, the ejection port 23 is lowered to the inside of the chamber to prevent mixture of bubbles into the upstream side of the venous side circuit 51.

The ejection port 23 of the inlet pipe 21 is provided along an inner peripheral surface 26 of the cap body 25, and has an opening facing in the circumferential direction of the inner peripheral surface 26. For instance, a lower wall 21A is formed at the lower end of the inlet pipe 21 and its side wall is cut out, forming the ejection port 23. For instance, the ejection port 23 faces parallel with the tangential direction of the inner peripheral surface 26. A cut surface 21B of the ejection port 23 is formed so as to be parallel with the radial direction of the inner peripheral surface 26.

Since the ejection port 23 is provided in the inner peripheral surface 26 of the cap body 25 and facing in the circumferential direction, the flow of the liquid (for example, blood or saline solution) flowing out from the ejection port 23 becomes a swirl flow along the inner peripheral surface 26. Since the liquid flow in the air trap chamber 10 becomes a swirl flow, retention of the liquid in the air trap chamber 10 is suppressed as compared with the case where a specific flow is not formed.

The first connection flange 27 is coupled to the lower end of the cap body 25. The first connection flange 27 is, for example, a cylindrical member coaxial with the cap body 25 and has an inner diameter made larger (expanded) than the inner diameter of the cap body 25.

As shown with reference to FIGS. 3, 5, and 7, the housing 30 is a generally cylindrical member having the second connection flange 32 at one end (upper end) defined with respect to the central axis C1 of the chamber body 12 and the outlet pipe 33 at the other end (lower end). The lower end of the outlet pipe 33 is the outlet 31. The outlet 31 is coupled to a connector (not shown in the drawing) on the upstream side of the venous side circuit 51, and passes the liquid (for example, blood or saline solution) in the air trap chamber 10 to the venous side circuit 51.

The housing 30 has the second connection flange 32, a tapered portion 35, a housing body 34, and the outlet pipe 33 in this order from the cap 20 side downward.

The second connection flange 32 is a cylindrical section to be locked in the first connection flange 27 of the cap 20. For instance, as illustrated in FIGS. 3 and 7, the two flanges are locked together so that the inner peripheral surface of the first connection flange 27 of the cap 20 and the outer peripheral surface of the second connection flange 32 of the housing 30 face each other. For instance, the inner diameter D1 of the second connection flange 32 is made equal to the inner diameter of the cap body 25. The inner diameter D1 of the second connection flange 32 is made larger than the inner diameter D2 of the housing body 34.

When the inner peripheral surface of the second connection flange 32 and the inner peripheral surface of the housing body 34 are tapered so that the diameter decreases toward the outlet 31, their maximum diameters may be set to the inner diameters D1 and D2.

The housing body 34 is, for example, a long cylindrical section that extends in the direction of the central axis C1 of the chamber body 12. The filter 40, which is attached to the outlet pipe 33 and captures a fixed object such as a thrombus, is contained in the housing body 34. The outlet pipe 33 is coupled to the lower end of the housing body 34.

The tapered portion 35 is formed between the second connection flange 32 and the housing body 34. The tapered portion 35 is a connection portion that connects the second connection flange 32 having a relatively large diameter and the housing body 34 having a relatively small diameter. As shown by its name, the tapered portion 35 is gradually narrowed from the second connection flange 32 toward the housing body 34. To be specific, the tapered portion 35 has an inner diameter gradually reduced from its upper end; that is, the inner diameter D1 of the point of connection to the second connection flange 32, to the lower end; that is, the inner diameter D2 of the point of connection to the housing body 34. As will be described later, a connection region 42 is defined by the tapered portion 35.

Figure 6:
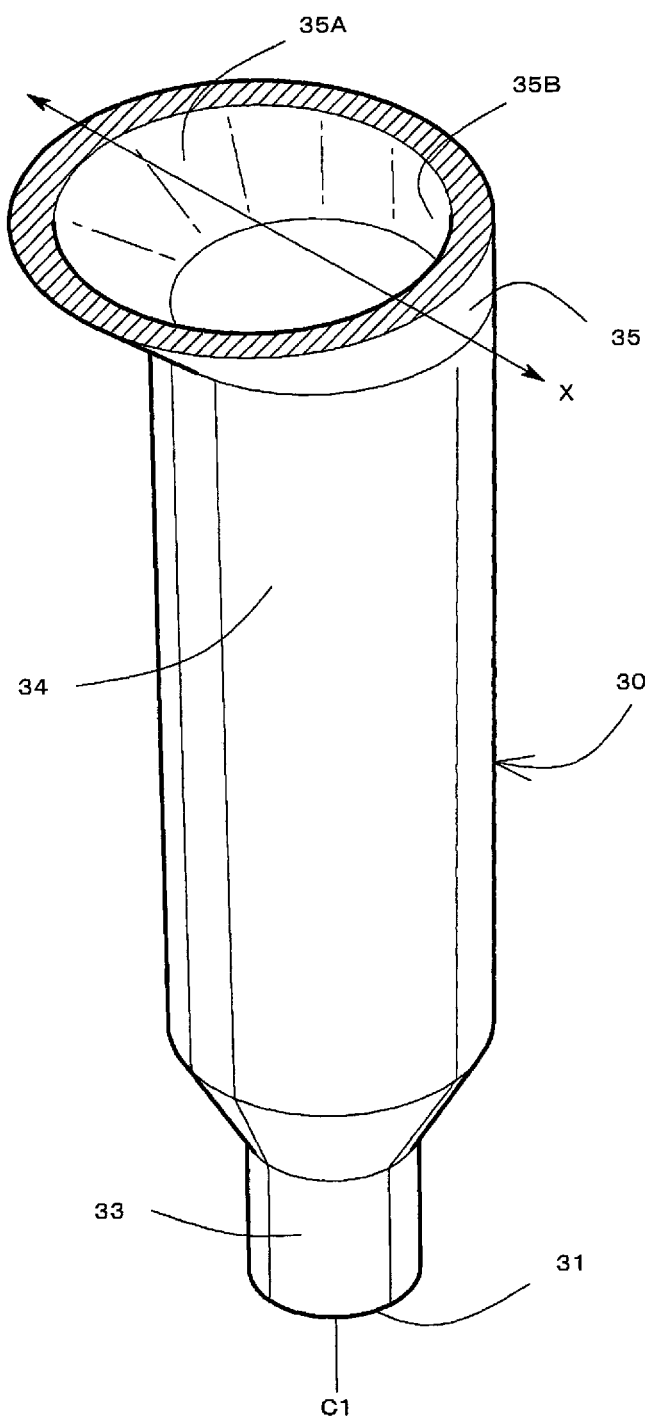
FIG. 6 is a perspective view illustrating an inclined surface of a tapered portion that constitutes a connection region.

As illustrated in FIGS. 6 and 7, the inner peripheral surface of the tapered portion 35 (and thus the connection region 42) may have a cross-section that is tapered toward one side. In other words, there may be formed an area where an inclined surface 35A is formed along the circumferential direction and an area where the inclined surface 35A ends and becomes a vertical surface 35B that is parallel with the inner peripheral surface of the second connection flange 32 (and thus the upper region 41).

FIG. 6 shows an example where the second connection flange 32 is removed from the housing 30. As illustrated in this drawing, the inner peripheral surface of the tapered portion 35 is formed into an oblique circular truncated cone shape including the vertical surface 35B.

For instance, considering the X axis that passes through the center of the cross-section circle from the position where the vertical surface 35B is formed, its inner surface is an inclined surface from the vertical surface 35B along the circumferential direction, and the inclination angle at the point facing the vertical surface 35B along the X axis is the acute angle closest to the X axis. In other words, since the central axis C1 and the X axis in FIG. 3 are orthogonal to each other, the inclination angle at the point is an angle lying on an axis or a plane perpendicular to the central axis C1.

Since the inner peripheral surface of the tapered portion 35 gradually inclines in the circumferential direction from the vertical surface 35B (so that the inclined surface is laid down) in this way, the flow of the swirl flow along the inner peripheral surface of the cap body 25 is smoothly guided by the inclined surface 35A. This makes it possible to change the direction of the flow with the inclined surface 35A of the tapered portion 35 while maintaining the force of the swirl flow, as compared to, for example, the case where a wall orthogonal to the flow direction is provided.

In addition, as compared to the case where the inclined surface 35A is provided on the entire peripheral portion of the inner peripheral surface of the tapered portion 35, in the case where the inclined surface 35A is provided on a part of the peripheral portion thereof, the inclined surface 35A can be laid down to a greater extent (inclined toward the horizontal side) when the inner diameter D1 of the upper region 41 and the inner diameter D2 of the lower region 43 are fixed.

For an index indicating the gradient of the inclined surface, the maximum inclination angle of the tapered portion 35 is used as a representative value which is represented by inclination angle α. In other words, the angle to the axis and plane perpendicular to the central axis C1 of the chamber body 12 is the inclination angle α. FIG. 7 illustrates a cross-sectional view along line A-A in FIG. 2, including the maximum inclination angle α of the tapered portion 35. In the example shown in this drawing, the inclination angle α is 42°.

In addition, since the diameter of the tapered portion 35, which decreases from the second connection flange 32 toward the housing body 34, is uneven along the radial direction, the opening axis C2 of the inlet pipe 21 of the cap 20 and the opening axis C1 of the outlet pipe 33 can be non-coaxial and separated from each other.

In other words, as described above, the opening axis C2 of the inlet pipe 21 is provided off-axis from the central axis C3 of the first connection flange 27 which is the central axis of the cap 20. In addition, since the decreasing diameter of the tapered portion 35 is uneven along the radial direction, the opening axis C1 of the outlet pipe 33 can be provided off-axis from the central axis C3 of the second connection flange 32.

For instance, as shown in FIG. 7, when the opening axis C2 of the inlet pipe 21 and the opening axis C1 of the outlet pipe 33 are aligned on the same plane with the central axis C3 of the first and second connection flanges 27 and 32 therebetween, the opening axis C2 of the inlet pipe 21 and the opening axis C1 of the outlet pipe 33 are separated in the vertical direction.

Since the opening axis C2 of the inlet pipe 21 is provided off-axis from the opening axis C1 of the outlet pipe 33, it is possible to suppress the phenomenon in which bubbles flowing back from the outlet pipe 33 enter the inlet pipe 21 when rising due to buoyancy. As a result, it is possible to suppress the phenomenon in which backflowing bubbles enter the arterial side circuit 50 and the blood purifier 54 located upstream from the air trap chamber 10.

Referring to FIG. 7, the chamber body 12 is divided into multiple regions in which a liquid (example, blood or saline solution) flows, depending on the configuration, particularly the inner diameter of each part of the cap 20 and the housing 30. To be specific, it can be divided into, from the cap 20 side, an upper region 41, the connection region 42, and a lower region 43.

The upper region 41 extends from the inner surface 28A of the top wall 28 of the cap 20 to the inlet pipe 21 and is defined by the top wall 28, the cap body 25, and the second connection flange 32 of the housing 30. The diameter D1 (inner diameter) of the inner peripheral surface of the region is larger than the inner diameter D2 of the lower region 43 (D1>D2).

The lower region 43 is coupled to the outlet pipe 33 and is defined by the housing body 34. The inner diameter D2 of the lower region 43 is smaller than the inner diameter D1 of the upper region 41.

The connection region 42 is a region that connects the upper region 41 and the lower region 43, and is defined by the tapered portion 35 of the housing 30. The inner peripheral surface is gradually reduced along the inclined surface 35A from the inner diameter D1 of the point of connection to the upper region 41 to the inner diameter D2 of the point of connection to the lower region 43.

<Flow of Liquid in Air Trap Chamber>

Figure 8:
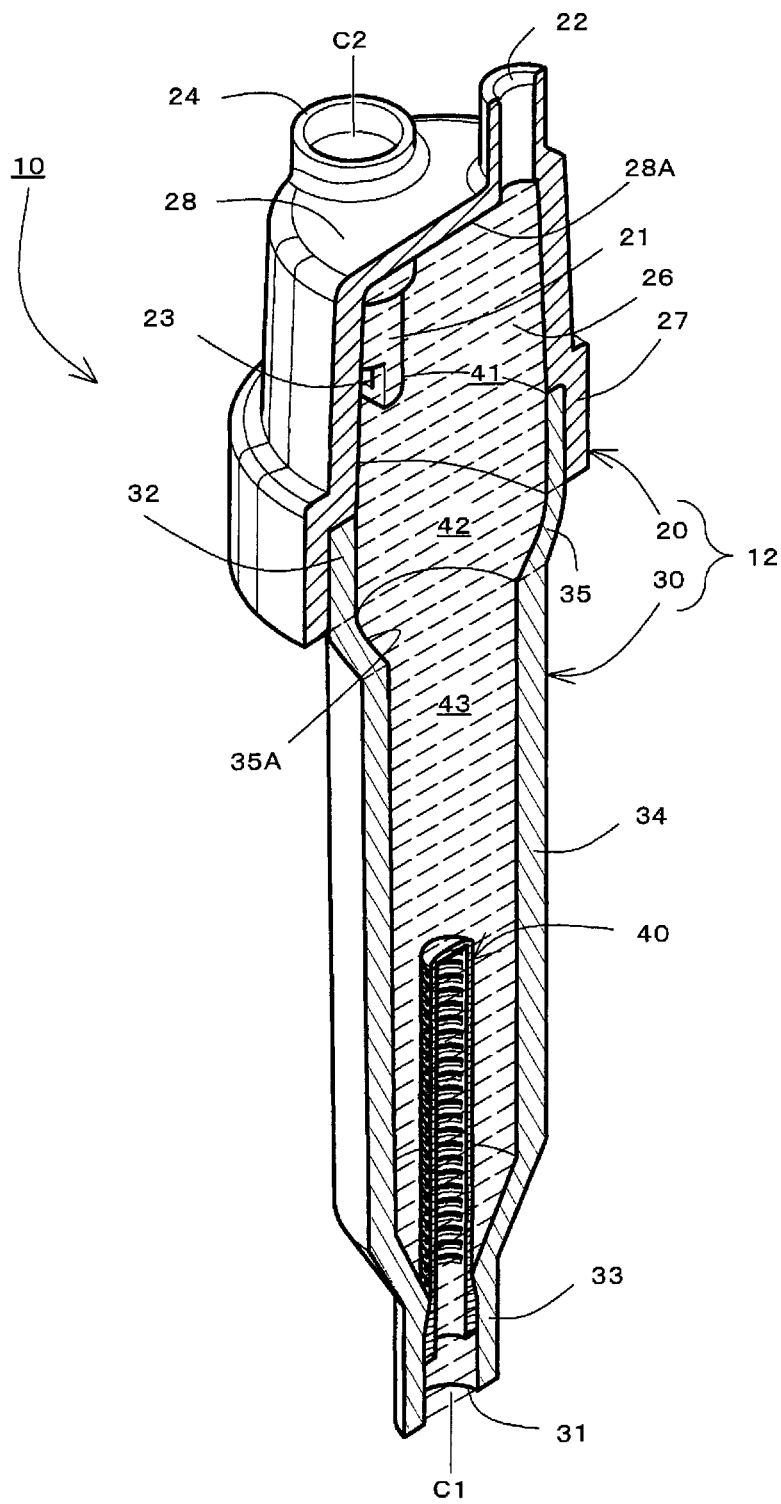
FIG. 8 is a perspective sectional view illustrating the air trap chamber according to the embodiment during use.
Figure 9:
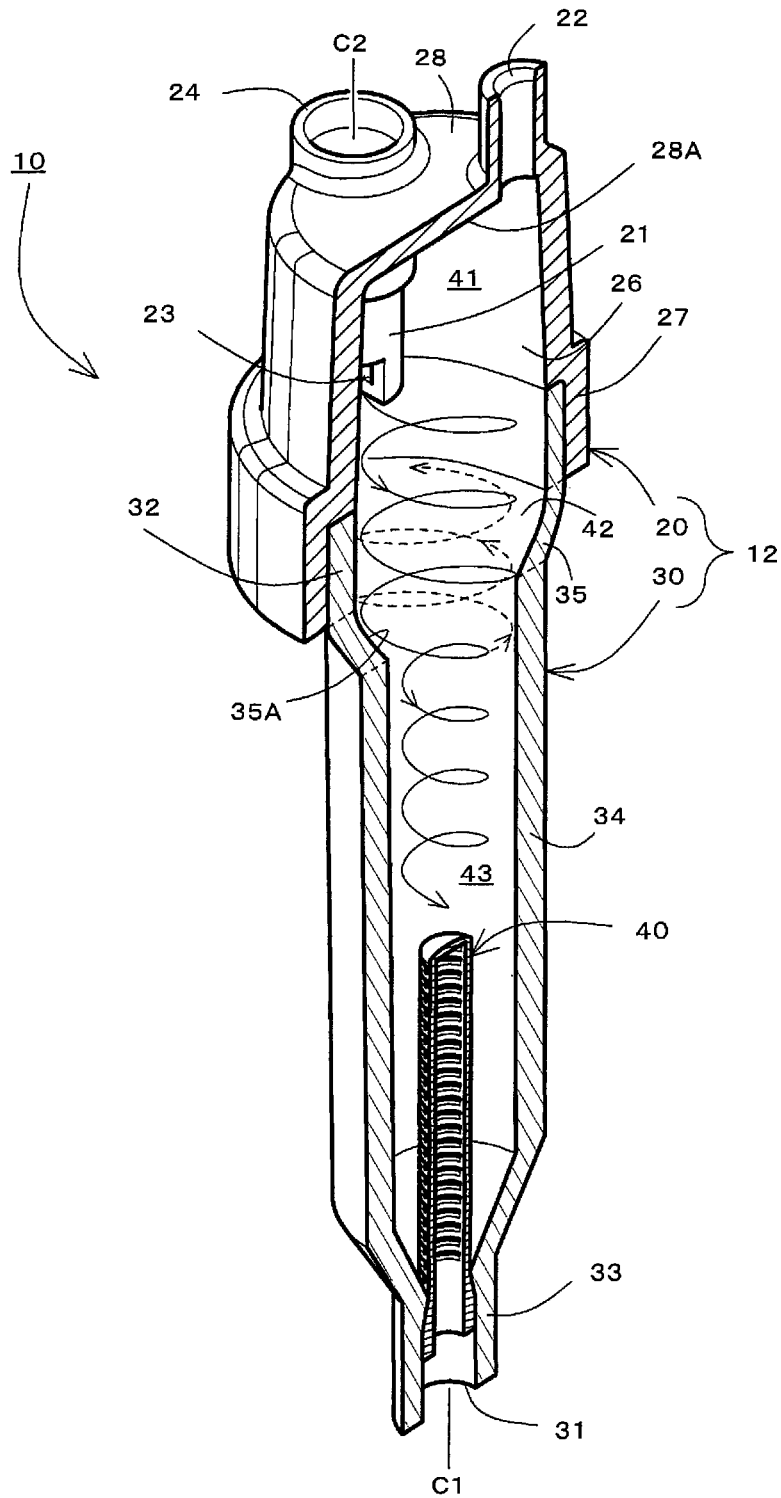
FIG. 9 is a diagram illustrating the overall flow in the air trap chamber according to the embodiment.
Figure 10:
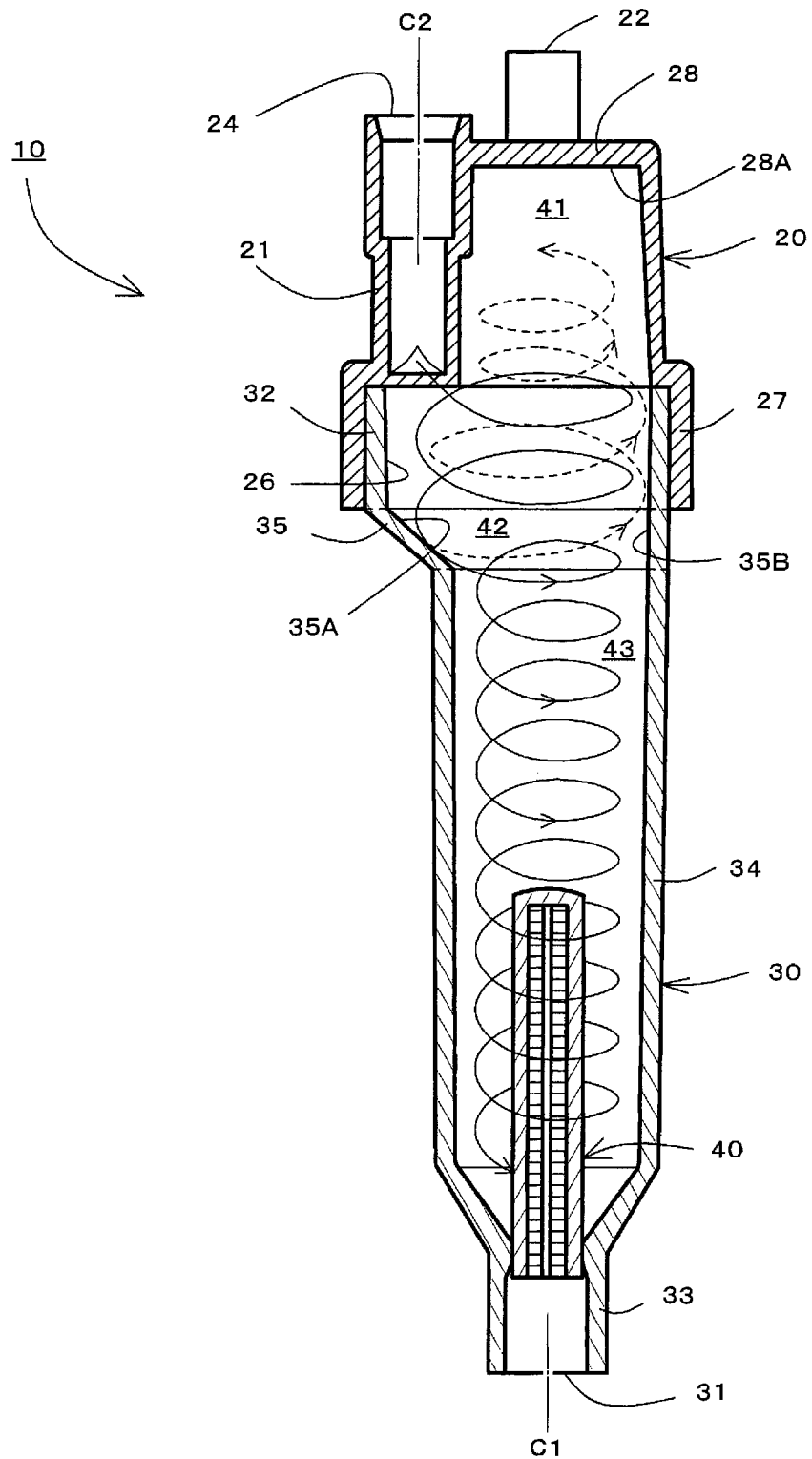
FIG. 10 is a cross-sectional view along line A-A in FIG. 2, illustrating the overall flow in the air trap chamber according to the embodiment.

With reference to FIGS. 8 to 10, the liquid (for example, blood or saline solution) in the air trap chamber 10 according to this embodiment will be described. FIG. 8 illustrates the state of the air trap chamber 10 during dialysis treatment. The air trap chamber 10 may be a so-called airless chamber, and the upper region 41, the connection region 42, and the lower region 43 of the inner space of the chamber body 12 are filled with a liquid as shown by the hatching with dashed lines in the drawing.

With the chamber body 12 filled with the liquid as described above, the liquid further flows in through the ejection port 23. Since the ejection port 23 is provided on the inner peripheral surface 26 of the cap 20 and facing in the circumferential direction as described above, the flow of the liquid flowing from the ejection port 23 becomes a swirl flow along the inner peripheral surface 26 of the upper region 41 as illustrated by the solid line in FIG. 9.

The swirling liquid flows along the inner peripheral surface 26 from the upper region 41 into the connection region 42. At this time, the direction of at least part of the swirl flow is changed along the inclined surface 35A of the connection region 42. To be specific, the decreasing diameter in the connection region 42 and the direction of the inclined surface 35A generate the upward swirl flow component indicated by the dashed lines in FIGS. 9 and 10.

Due to the upward swirl flow, the exchange of liquid in the upper region 41, particularly above the ejection port 23, is promoted. As the upward swirl flow is generated on the inclined surface 35A as described above, the retention of the liquid in the portion of the upper region 41 above the ejection port 23 is suppressed.

When the direction of the flow on the inclined surface 35A is changed, the inclined surface 35A is gradually inclined along the circumferential direction, from the vertical surface 35B continuous with the inner peripheral surface 26 of the upper region 41 as described above. Hence, the liquid smoothly flows from the inner peripheral surface 26 to the inclined surface 35A, and while the force of this flow is maintained, an upward swirl flow can be generated from at least part of the flow.

<Air Trap Chamber According to Modified Example of this Embodiment>

Figure 11:
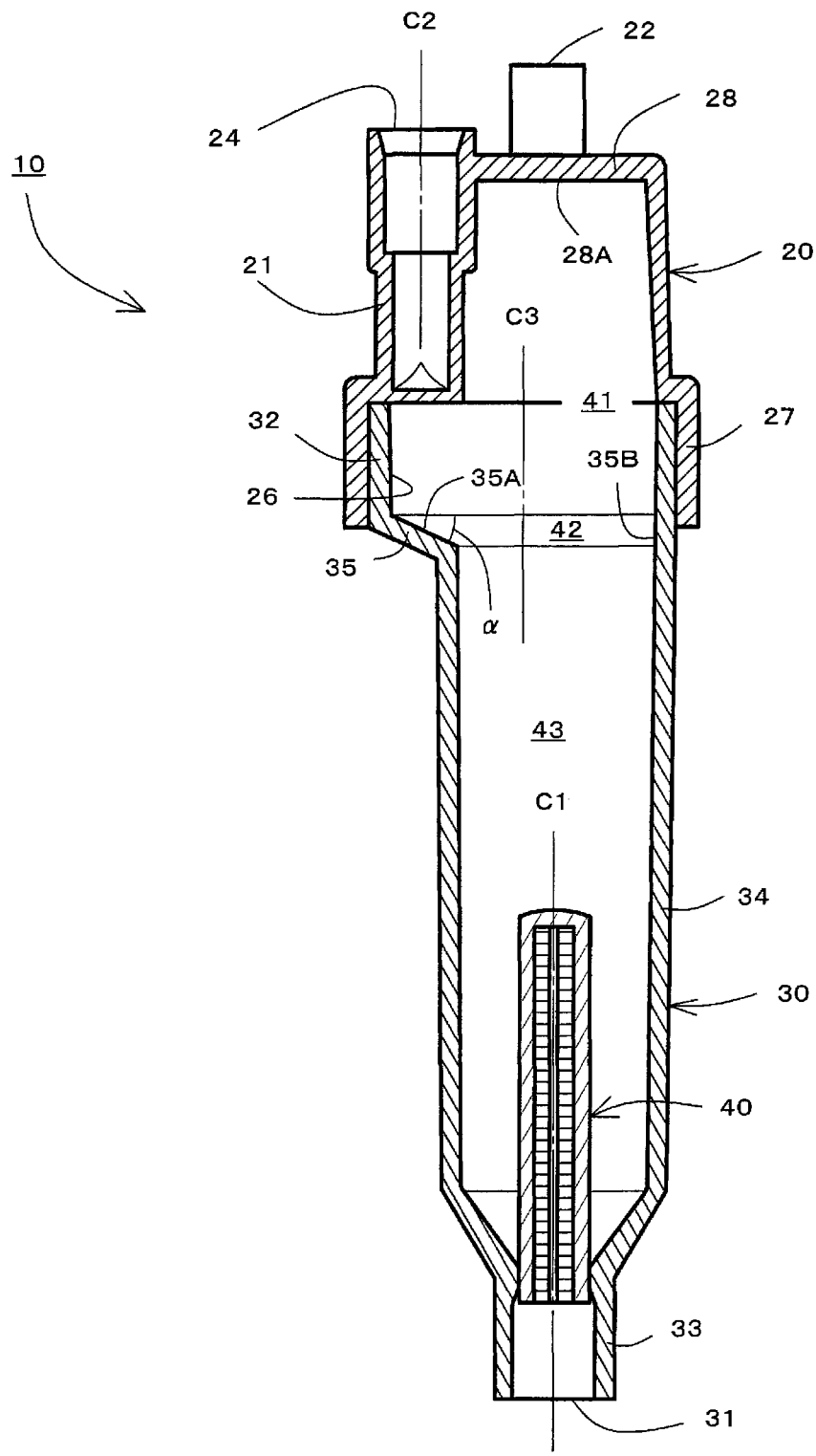
FIG. 11 is a diagram illustrating the same cross section as in the cross-sectional view along line A-A in FIG. 2 related to a first modified example of the air trap chamber according to the embodiment (inclination angle of 25°).
Figure 12:
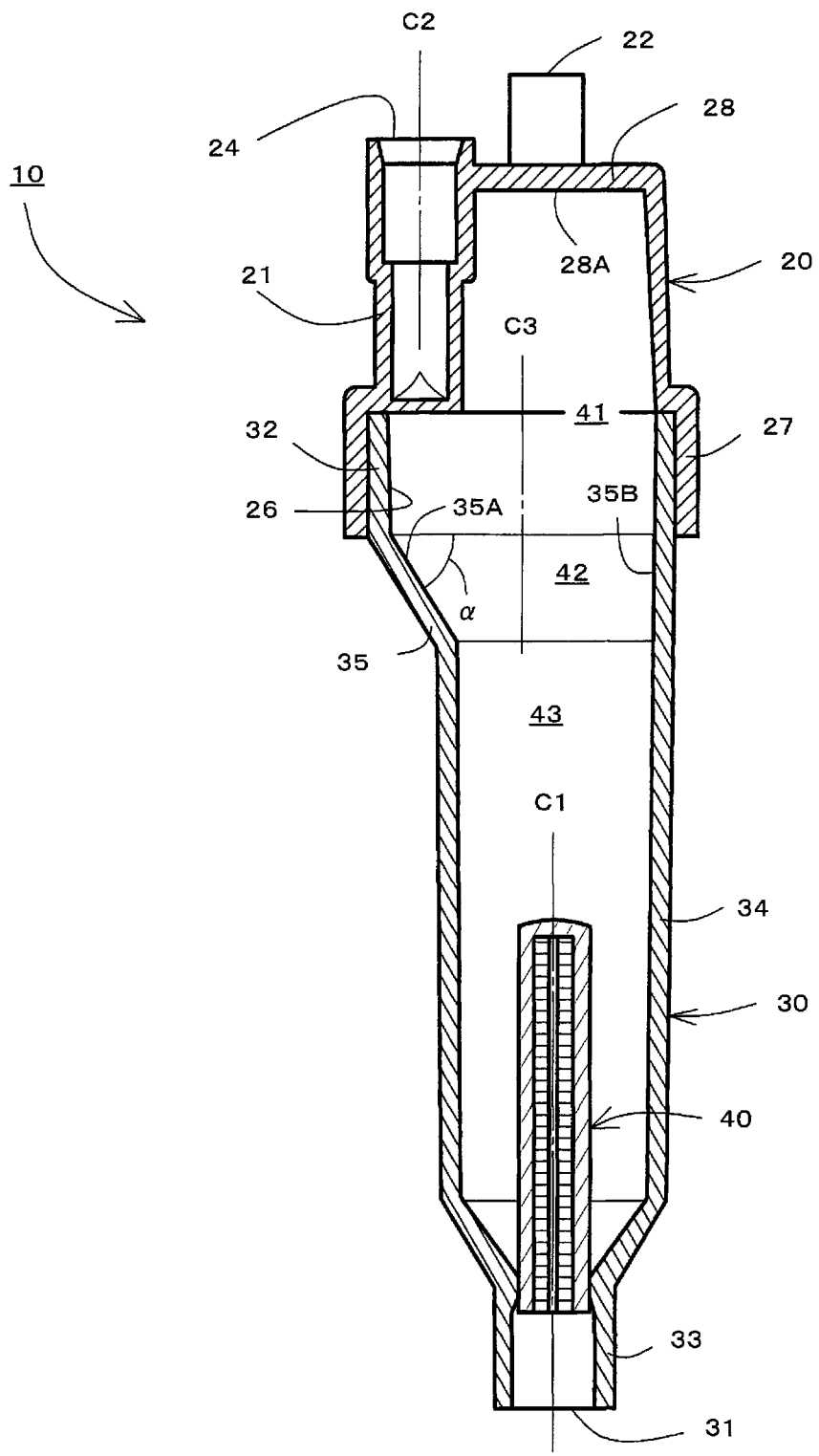
FIG. 12 is a diagram illustrating the same cross section as in the cross-sectional view along line A-A in FIG. 2 related to a second modified example of the air trap chamber according to the embodiment (inclination angle of 58°).
Figure 13:
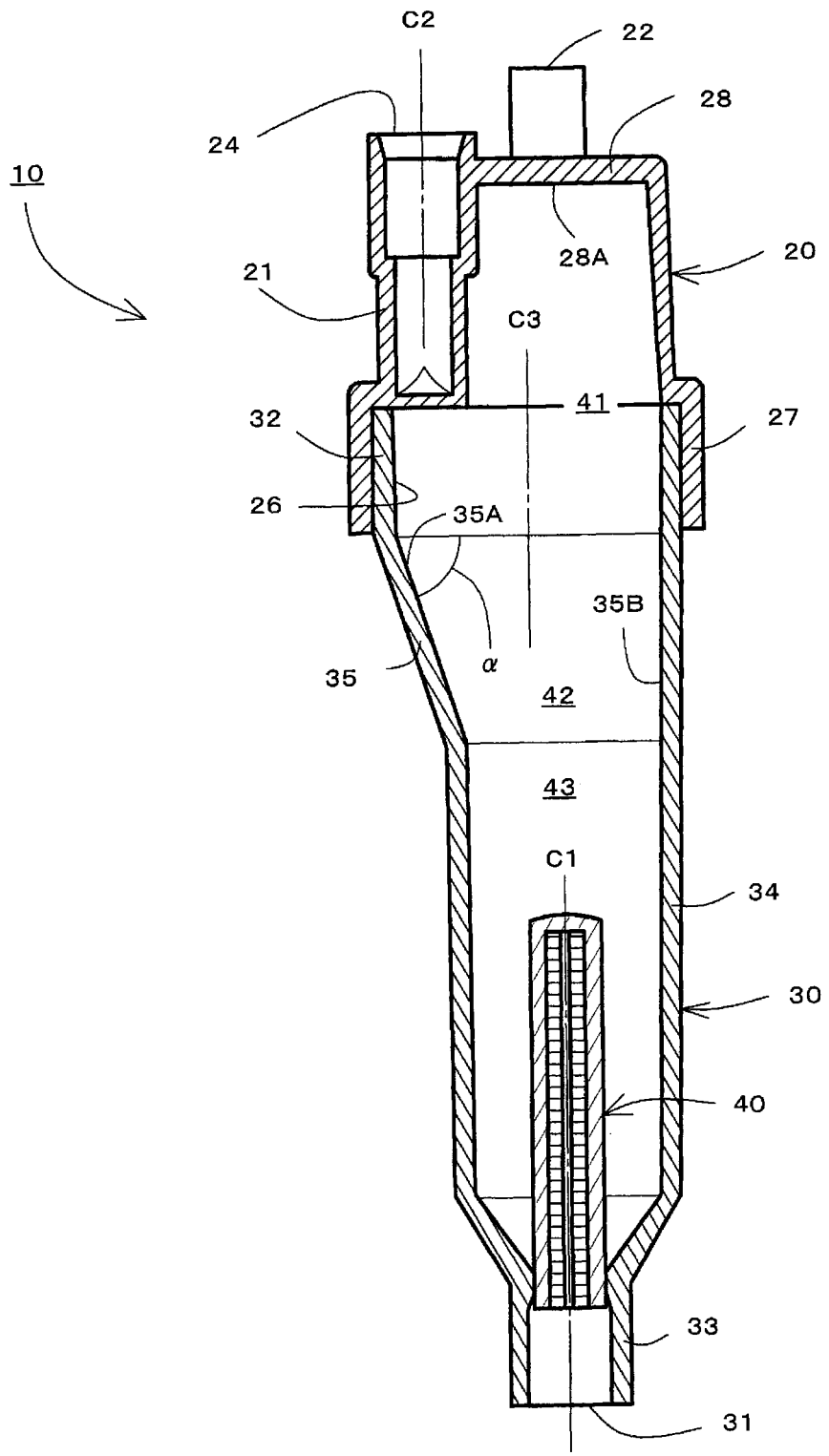
FIG. 13 is a diagram illustrating the same cross section as in the cross-sectional view along line A-A in FIG. 2 related to a third modified example of the air trap chamber according to the embodiment (inclination angle of 72°).

In the aforementioned embodiment, the inclination angle $\alpha$ of the tapered portion 35 is 42°; however, various other modifications can be made. For instance, since the direction of at least part of the swirl flow can be changed along the inclined surface 35A as described above, it is qualitatively $0°<\alpha<90°$. For instance, in the first modified example illustrated in FIG. 11, the inclination angle $\alpha$ is 25°. In the second modified example illustrated in FIG. 12, the inclination angle $\alpha$ is 58°. In the first modified example illustrated in FIG. 13, the inclination angle $\alpha$ is 72°.

In the first to third modified examples, since the inclined surface 35A is provided between the upper region 41 and the lower region 43 as in the embodiment illustrated in FIG. 10, at least part of the liquid flowing from the inner peripheral surface 26 can be made, using the inclined surface 35A, to form an upward swirl flow while a decrease in the force of that flow is suppressed.

Here, to reduce the volume of the air trap chamber 10 according to this embodiment and the first to third modified examples, it is necessary to prevent bubble leakage, the phenomenon in which bubbles escape from the outlet 31. Therefore, the present inventors conducted a test on the air trap chamber 10 according to this embodiment and the first to third modified examples for checking bubble leakage.

In the test, the capacity (priming volume, hereinafter referred to as PV) of the air trap chamber 10 according to the first modified example ($\alpha=25°$) was set to 16.3 mL. The PV of the air trap chamber 10 according to this embodiment was set to 16.5 mL. The PV of the air trap chamber 10 according to the second modified example ($\alpha=58°$) was set to 16.9 mL. The PV of the air trap chamber 10 according to the third modified example ($\alpha=72°$) was set to 17.6 mL.

Figure 14:
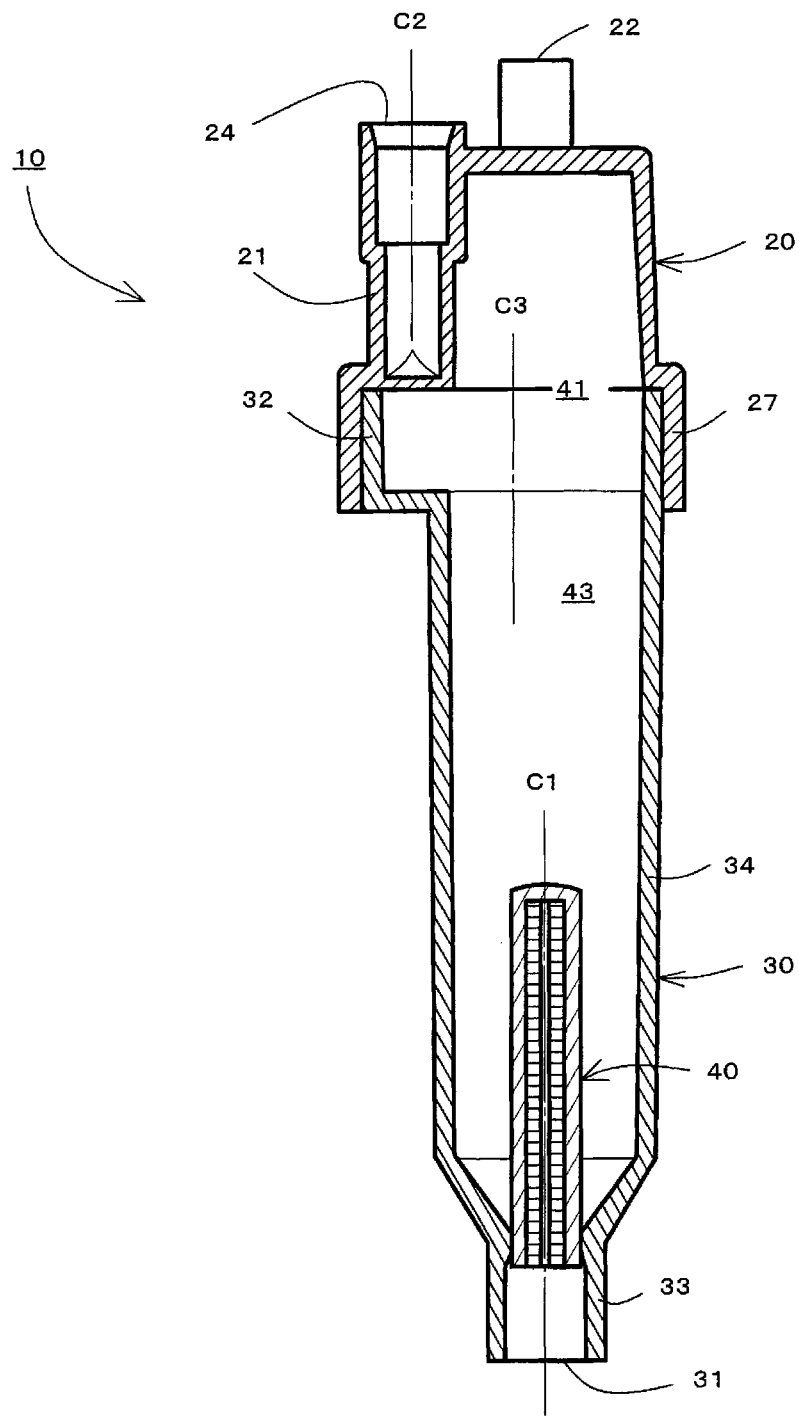
FIG. 14 is a diagram illustrating the same cross section as in the cross-sectional view along line A-A in FIG. 2 related to the air trap chamber according to a comparative example (inclination angle of 0°).

In this test, for a comparative example, an air trap chamber 10 having no inclined surface 35A was prepared as illustrated in FIG. 14. The PV of the chamber was 16.0 mL.

During the test, deaerated tap water was supplied to the inlet 24 of each air trap chamber 10 using a roller pump. The supply rates were 400 mL/min and 600 mL/min.

In addition, air was mixed into the air trap chamber 10 from the air vent 22 using a syringe. The amounts of air mixed were 0.3 µL and 15 µL for each air trap chamber 10. When air was mixed in the air trap chamber 10, the flow of tap water was once stopped, and the supply of tap water was restarted after mixing.

In addition, a bubble detection unit was connected to the outlet 31 of the air trap chamber 10. Each air trap chamber 10 was then tested three times for each amount of tap water supplied and amount of air mixed, for determining the presence or absence of bubbles using a bubble detection unit. In detecting bubbles, when the amount of air mixed using the syringe was 0.3 µL, the threshold of the bubble detection signal used by the bubble detection unit was set to 0.3 µL, and when the amount of air mixed was 15 µL, the threshold of the bubble detection signal used by the bubble detection unit was set to 15 µL. Table 1 shows the test results below.

TABLE 1

| Sample name (inclination angle α) | PV [mL] | Liquid flow rate: 400 mL/min | | Liquid flow rate: 600 mL/min | |
|---|---|---|---|---|---|
| | | Bubble injection rate 0.3 µL | Bubble injection rate 15 µL | Bubble injection rate 0.3 µL | Bubble injection rate 15 µL |
| First modified example (25°) | 16.3 | ○ | ○ | ○ | ○ |
| Embodiment (42°) | 16.5 | ○ | ○ | ○ | ○ |

TABLE 1-continued

|  |  | Liquid flow rate: 400 mL/min | | Liquid flow rate: 600 mL/min | |
| --- | --- | --- | --- | --- | --- |
| Sample name (inclination angle α) | PV [mL] | Bubble injection rate 0.3 μL | Bubble injection rate 15 μL | Bubble injection rate 0.3 μL | Bubble injection rate 15 μL |
| Second modified example (58°) | 16.9 | ○ | ○ | ○ | ○ |
| Third modified example (72°) | 17.6 | ○ | ○ | ○ | ○ |
| Comparative example (0°) | 16 | x | ○ | x | ○ |

In Table 1, the circle symbol indicates the case where no detection signal was output from the bubble detector in the three tests, and the X symbol indicates the case where a detection signal was output from the bubble detector in any one of the three tests. As illustrated in Table 1, in the air trap chamber 10 according to this embodiment and the first to third modified examples, when the inclination angle α is greater than or equal to 25° and less than or equal to 72°, bubble leakage can be effectively prevented.

Figure 15:
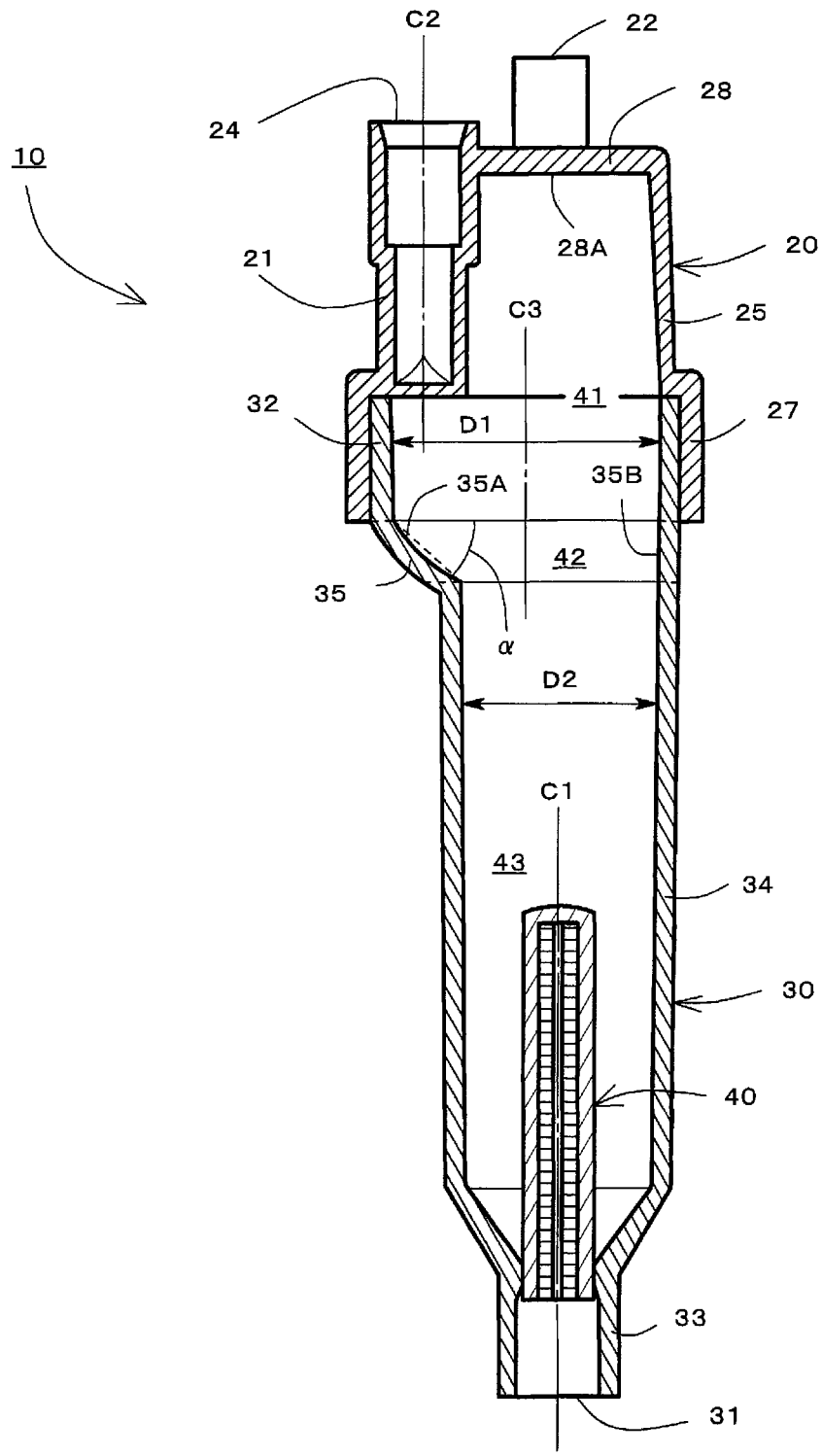
FIG. 15 is a diagram illustrating the same cross section as in the cross-sectional view along line A-A in FIG. 2 related to the fourth modified example of the air trap chamber according to the embodiment (concave).
Figure 16:
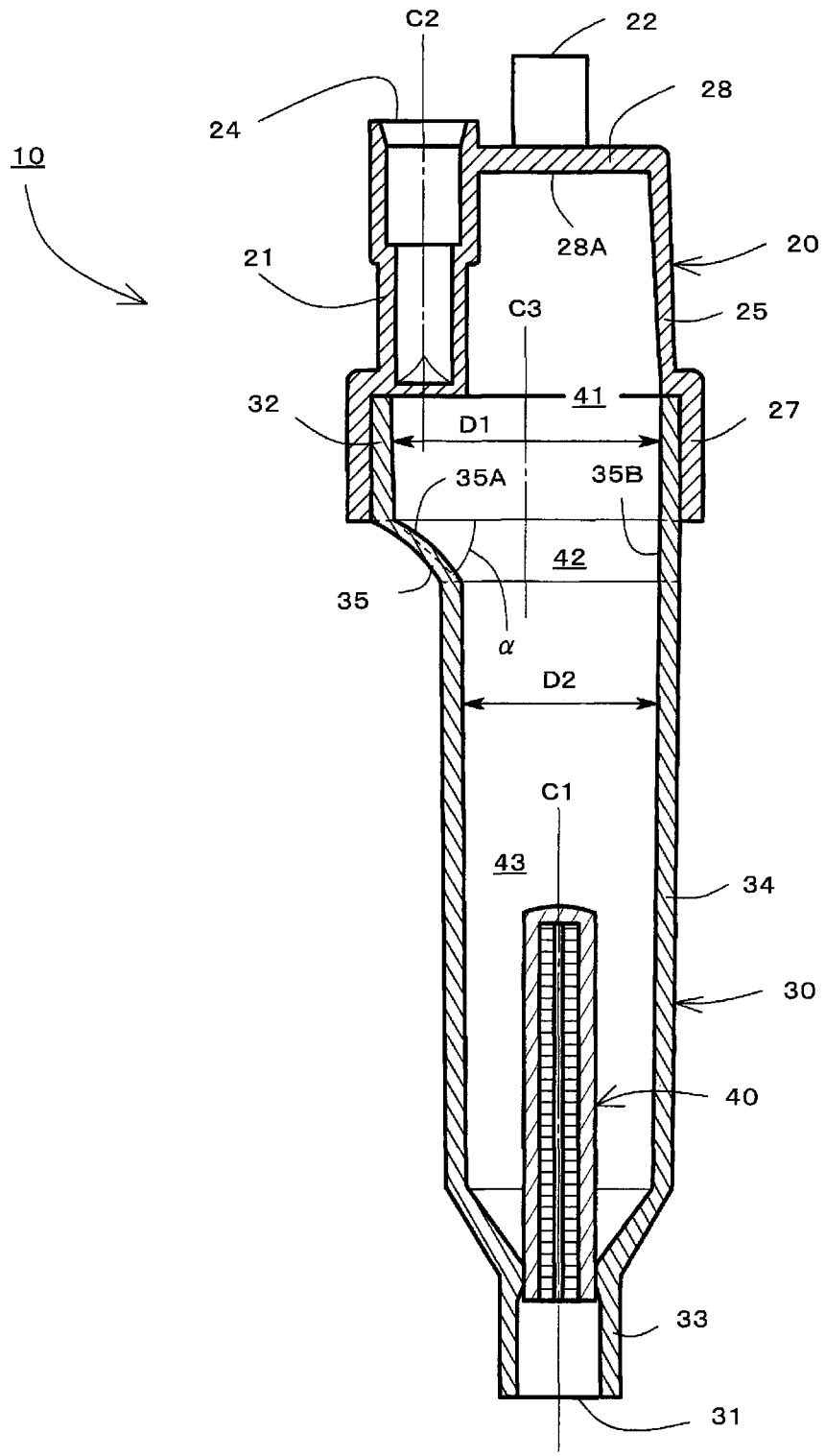
FIG. 16 is a diagram illustrating the same cross section as in the cross-sectional view along line A-A in FIG. 2 related to a fifth modified example of the air trap chamber according to the embodiment (convex).

In the aforementioned embodiment, the connection region 42; that is, the inclined surface 35A of the tapered portion 35, has a linear cross section; however, this is not necessarily the case. For instance, as in the fourth modified example shown in FIG. 15, the inclined surface 35A may be a concave curved surface projecting radially outward from the central axis C1 of the chamber body 12. Moreover, as in the fifth modified example shown in FIG. 16, the inclined surface 35A may be a convex curved surface projecting radially inward with respect to the central axis C1 of the chamber body 12.

When the inclined surface 35A is a concave curved surface or a convex curved surface, the inclination angle α may be defined as follows. In other words, the upper end of the tapered portion 35; that is, the point of the inclined surface 35A at the boundary with the upper region 41 and the lower end of the tapered portion 35; that is, the point of the inclined surface 35A at the boundary with the lower region 43, are connected. In relation to the resulting straight line, the angle to the axis and plane perpendicular to the central axis C1 of the chamber body 12 is the inclination angle α. With this definition, when the inclined surface 35A is a concave curved surface or a convex curved surface, the inclination angle α is preferably greater than 0° and less than 90°. The inclination angle α is more preferably greater than or equal to 25° and less than or equal to 72°.

REFERENCE SIGNS LIST

10 Air trap chamber, 12 Chamber body, 20 Cap, 21 Inlet pipe, 22 Air vent, 23 Ejection port, 24 Inlet, 25 Cap body, 26 Inner peripheral surface of upper region, 27 First connection flange, 28 Top wall of cap body, 28A Inner surface of top wall, 30 Housing, 31 Outlet, 32 Second connection flange, 33 Outlet pipe, 34 Housing body, 35 Tapered portion, 35A Inclined surface, 35B Vertical surface, 40 Filter, 41 Upper region, 42 Connection region, 43 Lower region, 50 Arterial side circuit, 51 Venous side circuit, 54 Blood purifier, 55 Dialyzer.

The invention claimed is:

1. An air trap chamber comprising:
a chamber body that has a generally cylindrical shape and has one end defined with respect to a central axis and covered with a top wall having an inlet, and the other end having an outlet, so that a liquid flows down from the inlet to the outlet; and
an inlet pipe that extends from the inlet into the chamber body, and has an ejection port being an opening formed on a side of the inlet pipe and provided along the inner peripheral surface of the chamber body facing in a circumferential direction, wherein
the chamber body has the following regions in which liquid flows:
an upper region extending from the top wall inner surface to the inlet pipe,
a lower region connected to the outlet, and
a connection region connecting the upper region and the lower region,
the inner peripheral surface of the upper region has a larger diameter than the inner peripheral surface of the lower region, and
the inner peripheral surface of the connection region has an inclined surface formed by reducing the diameter from a point of connection to the upper region to a point of connection to the lower region.

2. The air trap chamber according to claim 1, wherein the inner peripheral surface of the connection region has an oblique circular truncated cone shape having a vertical surface parallel with the inner peripheral surface of the upper region.

3. The air trap chamber according to claim 1, wherein an angle of the inclined surface to a plane perpendicular to the opening axis of the outlet is greater than 0° and less than 90°.

4. The air trap chamber according to claim 1, wherein an angle of the inclined surface to a plane perpendicular to the opening axis of the outlet is greater than or equal to 25° and less than or equal to 72°.

5. The air trap chamber according to claim 1, wherein the inclined surface is a concave curved surface projecting radially outward from the central axis of the chamber body.

6. The air trap chamber according to claim 1, wherein the inclined surface is a convex curved surface projecting radially inward with respect to the central axis of the chamber body.

7. An extracorporeal circulation circuit that circulates removed blood and has a flow path to which the air trap chamber according to claim 1 is coupled.

8. The air trap chamber according to claim 1, further comprising an air vent disposed along an axis that extends parallel to a longitudinal axis along which the inlet extends and to a longitudinal axis along which the outlet extends.

* * * * *